(12) United States Patent
Tonami

(10) Patent No.: US 8,410,447 B2
(45) Date of Patent: Apr. 2, 2013

(54) PARTICLE RADIOTHERAPY APPARATUS

(75) Inventor: Hiromichi Tonami, Kyoto-fu (JP)

(73) Assignee: Shimadzu Corporation, Kyoto (JP)

( * ) Notice: Subject to any disclaimer, the term of this patent is extended or adjusted under 35 U.S.C. 154(b) by 104 days.

(21) Appl. No.: 13/124,279

(22) PCT Filed: Oct. 23, 2008

(86) PCT No.: PCT/JP2008/069227
§ 371 (c)(1),
(2), (4) Date: Apr. 14, 2011

(87) PCT Pub. No.: WO2010/046983
PCT Pub. Date: Apr. 29, 2010

(65) Prior Publication Data
US 2011/0198502 A1    Aug. 18, 2011

(51) Int. Cl.
*G01T 1/161* (2006.01)
(52) U.S. Cl. .................................. 250/363.02
(58) Field of Classification Search ............. 250/363.04, 250/363.02; 378/65
See application file for complete search history.

(56) References Cited

U.S. PATENT DOCUMENTS

| | | | |
|---|---|---|---|
| 2010/0128956 A1* | 5/2010 | Yamaya et al. | 382/132 |
| 2010/0172468 A1* | 7/2010 | Gregerson | 378/20 |
| 2011/0240867 A1* | 10/2011 | Tonami | 250/366 |
| 2011/0301449 A1* | 12/2011 | Maurer, Jr. | 600/411 |

OTHER PUBLICATIONS

Crespo et al., On the detector arrangement for in-beam PET for hadron therapy monitoring, Apr. 11, 2006, Phys. Med. Biol., vol. 51, 2143-2163.*
Tashima et al., A single-ring OpenPET enabling PET imaging during radiotherapy, Jul. 2, 2012, Phys. Med. Biol. vol. 57, 4705-4718.*
Kinouchi et al., Simulation Design of a Single-Ring OpenPET for In-Beam PET, 2011, IEEE Nuclear Science Symposium Conference Record, pp. 3481-3483.*
Yamaya, Taiga et al., "An Initial Investigation of Open PET Geometries", IEEE Nuclear Science Symposium Conference Record, 2007, No. 5, pp. 3688-3690.

* cited by examiner

*Primary Examiner* — Christine Sung
(74) *Attorney, Agent, or Firm* — Cheng Law Group, PLLC

(57) ABSTRACT

In a particle radiotherapy apparatus which has a passage for allowing movement of a particle beam, this invention provides a particle radiotherapy apparatus with high sensitivity for detection of annihilation radiation pairs even if there is a difference between a point where the particle beam loses energy and a position of a detector ring in a body axis direction of a patient. For the purpose of solving such a problem, the particle radiotherapy apparatus according to this invention includes an elliptic detector ring which is vertically long and is reversibly tiltable. Consequently, annihilation gamma ray pairs are detected with the single elliptic detector ring. Then, annihilation gamma ray pairs occurring inside the elliptic detector ring will be detected. In other words, all annihilation gamma ray pairs will impinge on the single elliptic detector ring at substantially right angles. This inhibits lowering of sensitivity for detection.

14 Claims, 11 Drawing Sheets (a)

(b)

Prior Art

Prior Art

PARTICLE RADIOTHERAPY APPARATUS

TECHNICAL FIELD

This invention relates to a particle radiotherapy apparatus for carrying out medical treatment by emitting a particle beam to a patient, and more particularly relates to a particle radiotherapy apparatus which can monitor an irradiation area of a particle beam during medical treatment.

BACKGROUND ART

In treatment of cancer, for example, a lesion of a patient may be irradiated with radiation. In such radiotherapy, a particle radiotherapy apparatus which uses a particle beam has been developed (see Nonpatent Document 1, for example).

Such a particle radiotherapy apparatus will be described. As shown in FIG. 15, a conventional particle radiotherapy apparatus 51 includes a top board 52 for supporting a patient M, a particle beam source 53 for emitting a particle beam, and a first detector ring 54 and a second detector ring 55 for detecting annihilation gamma ray pairs generating from inside the patient M. The particle beam source 53 is disposed in a position between the two detector rings 54 and 55. And the particle beam source 53 can move around the patient M, about the body axis of the patient M. That is, a gap provided between the two detector rings 54 and 55 serves as a passage of the particle beam.

The construction of the two detector rings 54 and 55 will be described. The first detector ring 54 is constructed of blockish radiation detectors 61 arranged in a ring form. As shown in FIG. 16, this radiation detector 61 has a scintillator 62 for converting the radiation into fluorescence, and a photomultiplier tube (hereinafter called photodetector) 63 for detecting the fluorescence. The scintillator 62 has rectangular parallelepiped-shaped scintillator crystals C arranged in three dimensions. The photodetector 63 can determine which scintillator crystals C have emitted the fluorescence. That is, the radiation detector 61 can specify where on the scintillator 62 the radiation is incident. Of the surfaces of the scintillator 62, the surface remotest from the photodetector 63 will be called the plane of incidence 62a for expediency.

Next, a sectional view of the conventional particle radiotherapy apparatus 51 is shown. As shown in FIG. 17, the two detector rings 54 and 55 in the conventional particle radiotherapy apparatus 51 have the radiation detectors 61 arranged simply. That is, the scintillators 62 are directed inward of the two detector rings 54 and 55. Specifically, the scintillators 62 are directed to the same positions in the body axis direction A of the patient M.

When carrying out radiotherapy with the particle radiotherapy apparatus 51, a particle beam is emitted from the particle beam source 53 to the patient M placed on the top board 52. The particle beam source 53 moves around the body axis of the patient M while emitting the particle beam, and continues emitting the particle beam to the patient M while changing irradiation angle. The particle beam loses energy in the body of the patient M. At this time, the nucleus located at the point where the particle beam loses energy is converted into a nuclide which causes β+ decay. This nucleus causes β+ decay and emits a positron.

The resulting positron encounters and annihilates with an electron present in the vicinity. At this time, a pair of annihilation gamma rays are produced, which move in 180° opposite directions. This annihilation gamma ray pair penetrate the patient M, and are detected by the two detector rings 54 and 55. The conventional particle radiotherapy apparatus 51 determines the location where this annihilation gamma ray pair have been produced, thereby to presume a point where the particle beam lost energy. Cells are destroyed adjacent the point where the particle beam lost energy. In this way, it can be found out whether the particle beam accurately aims at the lesion of the patient M. The annihilation gamma ray pairs are an example of radiation resulting from the particle beam.

In order to attain the object of determining the location where the annihilation gamma ray pair have been produced, both of the annihilation gamma ray pair must be detected. This is because the point of occurrence of the annihilation gamma ray pair is determined by obtaining a line (Line of Response: hereinafter referred to as LOR as appropriate) extending between two points where the annihilation gamma ray pair are detected.

[Nonpatent Document 1] "IEEE Nuclear Science Symposium Conference Record" (U.S.A.), November 2007, No. 5, p3688-3690

DISCLOSURE OF THE INVENTION

Problem to be Solved by the Invention

However, the conventional construction has the following drawback.

That is, according to the conventional construction, it is necessary to provide the passage for allowing movement of the particle beam source 53, which poses a problem that the sensitivity for detection of annihilation gamma ray pairs is not sufficient. That is, the sensitivity for detection of the annihilation gamma ray pairs falls victim to the restriction that the particle beam source 53 must always be in the same position as the position in the body axis direction A of the lesion of the patient M. Specifically, the sensitivity of the detector rings for detection of the annihilation gamma ray pairs depends greatly on the direction of incidence of the annihilation gamma ray pairs on the detector rings.

Supposing the positions of the first detector ring 54 and an annihilation point having produced an annihilation gamma ray pair are the same in the body axis direction A of the patient M, the annihilation gamma ray pair advance into the first detector ring 54 at substantially right angles to the body axis direction A. Then, as shown in FIG. 18(a), one of the gamma rays forming the annihilation gamma ray pair is incident on the plane of incidence 62a of the scintillator 62, and moves toward the photodetector 63. Then, since the gamma ray passes through the thick scintillator 62 in its movement toward the photodetector 63, the gamma ray is reliably converted into fluorescence, which constitutes high sensitivity for detecting the gamma ray.

The two detector rings 54 and 55 of the particle radiotherapy apparatus 51 are arranged clear of the passage through which the particle beam source 53 moves. Since the position in the body axis direction A of the lesion of the patient M and the particle beam source 53 must always be in the same position irrespective of revolution of the particle beam source 53, the point in the body axis direction A of the patient M at which the particle beam loses energy and the positions of the two detector rings 54 and 55 are different from each other. That is, an annihilation gamma ray pair advance into the first detector ring 54 from oblique directions with respect to the body axis direction A. Then, as shown in FIG. 18(b), a gamma ray does not necessarily move from the plane of incidence 62a of the scintillator 62 toward the photodetector 63, but may move toward a side surface of the scintillator 62. Then, part of the gamma rays constituting annihilation gamma ray pairs bypass central parts of the scintillators 62 and exit from side surfaces of the scintillators 62. Such gamma rays are never converted into fluorescence, and are not detected by the radiation detectors 61 after all.

That is, when an annihilation gamma ray pair advance into the first detector ring 54 from oblique directions with respect to the body axis direction A, the scintillators 62 have an insufficient thickness on paths of the gamma rays, at lateral ends in the body axis direction A. This is because the gamma rays incident on the planes of incidence 62a of the scintillators 62 bypass the central parts of the scintillators 62, and immediately move to side surfaces of the scintillators 62.

The gamma rays released from the patient M in the particle radiotherapy apparatus 51 are very small in quantity, compared with a PET (Positron Emission Tomography) apparatus which medicates a patient M with a radioactive substance which emits annihilation gamma ray pairs, and images a distribution of the latter, and its dose is about $\frac{1}{1000}$ to $\frac{1}{100}$ of the PET apparatus, for example.

That is, improving the sensitivity for detection of annihilation gamma ray pairs in the particle radiotherapy apparatus 51 leads to an accurate confirmation that the annihilation gamma ray pairs are produced in the lesion of the patient. This is a matter of great importance in developing the particle radiotherapy apparatus 51 which can carry out effective medical treatment.

The conventional construction includes the two detector rings 54 and 55. The two detector rings will increase the manufacturing cost of the particle radiotherapy apparatus 51. However, a single detector ring would be incapable of detecting both gamma rays of an annihilation gamma ray pair.

That is, in the particle radiotherapy apparatus 51, as shown in FIG. 19, a single detector ring may be sufficient as long as it can measure annihilation gamma rays advancing in a state of maintaining a position G in the body axis direction A of the patient M. However, the particle radiotherapy apparatus 51 is required to provide a passage for the particle beam, and therefore the radiation detector cannot be disposed in position G. That is, it is impossible to detect annihilation gamma rays advancing in the state of maintaining the position G. Instead, annihilation gamma ray pairs having directions of movement deviating from the above position G are detected. As shown in FIG. 19, one gamma ray of such an annihilation gamma ray pair advances forward in the body axis direction A of the patient M, while the other gamma ray advances backward in the body axis direction A of the patient M. It is impossible to detect such an annihilation gamma ray pair with a single detector ring. This is because the positions of the radiation detectors provided for the detector ring are the same positions with respect to the body axis direction A of the patient M. After all, the conventional construction cannot operate with a single detector ring.

This invention has been made having regard to the state of the art noted above, and its object is, in the particle radiotherapy apparatus which has a passage for allowing movement of a particle beam, to provide a particle radiotherapy apparatus with high sensitivity for detection of annihilation radiation pairs even if there is a difference between a point where the particle beam loses energy and a position of a detector ring in a body axis direction A of a patient M.

Means for Solving the Problem

To fulfill the above object, this invention provides the following construction.

A particle radiotherapy apparatus according to this invention comprises a detector ring constructed of an annular arrangement of radiation detectors formed by laminating, in one direction, scintillators with planes of incidence for receiving radiation and converting the radiation into fluorescence, light guides for receiving and transmitting the fluorescence, and photodetectors for detecting the fluorescence, and in addition thereto, an elongated top board inserted in an opening of the detector ring, and a particle beam emitting device for emitting a particle beam; the particle radiotherapy apparatus further comprising a detector ring tilting device for reversibly tilting the detector ring relative to the top board; wherein the detector ring, tilting device is arranged to tilt an upper end of the detector ring in One direction in a direction of extension of the top board, and to tilt a lower end of the detector ring in a direction opposite to the one direction in the direction of extension of the top board.

[Functions and Effects] The construction of this invention includes the detector ring tilting device for reversibly tilting the detector ring. Consequently, the detector ring is tilted relative to the top board. More particularly, the upper end of the detector ring is tilted in one direction in the direction of extension of the top board. The lower end of the detector ring is tilted in a direction opposite to the one direction in the direction of extension of the top board. The particle beam source emits a particle beam toward the top board. Therefore, the detector ring cannot be disposed in a position to interfere with travel of this particle beam. The construction of this invention can tilt the detector ring relative to the top board. This means that the positional relationship between the detector ring and particle beam is changeable. Therefore, since the detector ring can be moved away from the particle beam by tilting the detector ring according to this invention, it is possible to provide the particle radiotherapy apparatus which can detect annihilation radiation while emitting the particle beam.

Moreover, annihilation radiation pairs are detected with the single detector ring. Then, annihilation radiation pairs occurring inside the detector ring will be detected. In other words, all annihilation radiation pairs will impinge on the single detector ring at substantially right angles. This inhibits the lowering of the sensitivity for detection described using FIG. 18.

According to this invention, the upper end and lower end of the detector ring are tilted in opposite directions. Consequently, the predetermined area (lesion area of the patient) can always be located inside the opening of the detector ring irrespective of the tilting of the detector ring. The particle radiotherapy apparatus can create a map of occurrence distribution of annihilation radiation pairs for the inside of the opening of the detector ring. The lesion area of the patient being located inside the opening of the detector ring irrespective of the tilting of the detector ring means that an occurrence distribution of annihilation radiation pairs in the lesion area of the patient is acquirable also while the emitting particle beam. That is, according to this invention, it is not necessary to provide two detector rings as in the prior art, but annihilation radiation pairs can be detected fully only by providing the single detector ring. The particle radiotherapy apparatus with manufacturing cost sharply reduced as compared with the prior art can be provided since the manufacturing cost of the particle radiotherapy apparatus depends heavily on the number of radiation detectors mounted in the detector ring.

It is preferred that the above detector ring has an elliptic shape, and when the detector ring is tilted to a predetermined tilt angle, the radiation detectors provided for the detector ring are arranged along an imaginary cylinder having a direction of extension in agreement with the top board.

Furthermore, it is preferred that the detector ring is vertically long.

[Functions and Effects] According to the above construction, the detector ring has an elliptic shape which is vertically long. Moreover, at a predetermined tilt angle, the radiation detectors provided for the detector ring are in a characteristic arrangement. That is, the radiation detectors are arranged along the imaginary cylinder. The cylinder has an extending direction corresponding to the top board, and the shape provided by obliquely cutting this cylinder agrees with the elliptic shape of the detector ring. And the radiation detectors provided for the detector ring are also arranged along this imaginary cylinder. As the detector ring is tilted, the upper part and lower part of the detector ring approach the top board. However, according to the above construction, since the detector ring is vertically long, the detector ring reliably remains out of contact with the patient.

It is preferred that the above detector ring tilting device is arranged to tilt the detector ring about a central axis provided by a short axis of the detector ring having the elliptic shape, and a position of the short axis of the detector ring is constant irrespective of tilting of the detector ring.

[Functions and Effects] The above construction can provide the particle radiotherapy apparatus which can image the lesion of the patient reliably only by keeping in agreement the lesion of the patient and the short axis of the detector ring. That is, according to the above construction, the position of the short axis of the detector ring is constant irrespective of tilting of the detector ring. Thus, the short axis of the detector ring will always be located inside the opening of the detector ring irrespective of the tilting. Therefore, the above construction can provide the particle radiotherapy apparatus which can image the lesion of the patient more simply and reliably.

The above detector ring may be arranged to detect radiation resulting from the particle beam while being tilted by the detector ring tilting device.

The above detector ring may be arranged to detect radiation resulting from the particle beam after being tilted by the detector ring tilting device and in a state of maintaining the tilt angle.

[Functions and Effects] The above construction can provide the particle radiotherapy apparatus with high sensitivity for detection of annihilation radiation pairs. It is predicted that various nuclides are generated at points inside the body of the patient where the particle beam lost energy. The energies and characteristics of the radiation released by decay thereof are varied. It is possible that single photons which are not annihilation gamma ray pairs are released. Such single photons may be detected by the detector ring. These cause noise when imaging action positions of the particle beam using the annihilation gamma ray pairs. However, according to the above construction, tilting of the detector ring, including also the tilting direction, can be optimized. Specifically, the particle beam may be emitted while tilting the detector ring, for the purpose of determining a tilt of the detector ring. When a desired tilt of the detector ring has been determined, the particle beam may be emitted while maintaining the tilt angle.

Effects of the Invention

The construction of this invention includes the detector ring tilting device for reversibly tilting the detector ring. Consequently, the detector ring is tilted relative to the top board. The particle beam source emits a particle beam toward the top board. The construction of this invention can tilt the detector ring relative to the top board. Therefore, since the detector ring can be moved away from the particle beam by tilting the detector ring according to this invention, it is possible to provide the particle radiotherapy apparatus which can detect annihilation radiation while emitting the particle beam.

A map of occurrence distribution of annihilation radiation pairs can be created for the inside of the opening of the detector ring. The lesion of the patient can be located inside the opening of the detector ring, even when a particle beam is emitted, by tilting the detector ring. According to this invention, it is not necessary to provide two detector rings as in the prior art, but annihilation radiation pairs can be detected fully only by providing the single detector ring.

Figure 1:
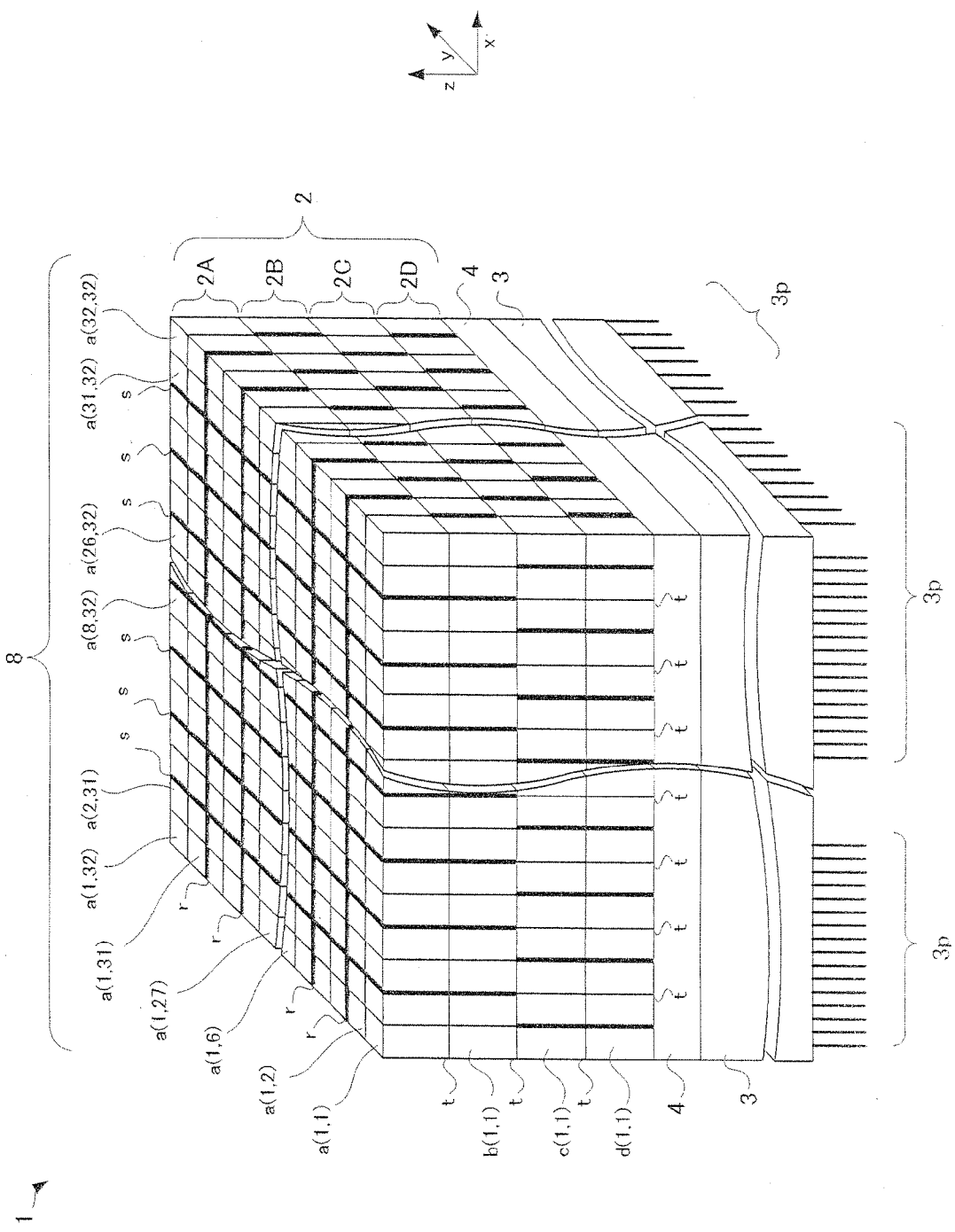
FIG. 1 is a perspective view of a radiation detector according to Embodiment 1.

DESCRIPTION OF REFERENCES 1 radiation detector
2 scintillator
3 photodetector
4 light guide
9 particle radiotherapy apparatus
10 top board
12 elliptic detector ring (detector ring)
13 particle beam source (particle beam emitting device)
15 tilt controller (detector ring tilting device)

BEST MODE FOR CARRYING OUT THE INVENTION

The best mode of particle radiotherapy apparatus according to this invention will be described hereinafter with reference to the drawings. Gamma rays in the following description are one example of radiation in this invention.

Embodiment 1

First, a construction of a radiation detector 1 according to Embodiment 1 will be described in advance of description of a particle radiotherapy apparatus according to Embodiment 1. FIG. 1 is a perspective view of a radiation detector according to Embodiment 1. As shown in FIG. 1, the radiation detector 1 according to Embodiment 1 includes a scintillator 2 formed of each of scintillator crystal layers laminated in z-direction in order of scintillator crystal layer 2D, scintillator crystal layer 2C, scintillator crystal layer 2B and scintillator crystal layer 2A, a photomultiplier tube (hereinafter called photodetector) 3 disposed on a lower surface of the scintillator 2 and having a position specifying function for detecting fluorescence emitted from the scintillator 2, and a light guide 4 disposed in a position interposed between the scintillator 2 and photodetector 3 for receiving and transmitting the fluorescence. Therefore, each of the scintillator crystal layers is laminated in a direction toward the photodetector 3. The scintillator crystal layer 2A serves as a plane of incidence 8 of radiation on the scintillator 2. In other words, the surface opposed to the photodetector 3 among the surfaces of the scintillator 2 is the plane of incidence. Each of the scintillator crystal layers 2A, 2B, 2C and 2D is optically coupled, and transmission members t are formed between the respective layers. As a material for these transmission members t, a thermosetting resin such as silicone resin may be used. The scintillator crystal layer 2A serves as a light receiver of gamma rays emitted from a radiation source, and is formed of blockish scintillator crystals arranged in a two-dimensional matrix form having 32 crystals in x-direction and 32 crystals in y-direction with scintillator crystal a(1, 1) acting as the basis. That is, scintillator crystal a(1, 1)-scintillator crystal a(1, 32) are arranged in y-direction to form a scintillator crystal array.

The scintillator crystal layer 2A is formed of 32 such scintillator crystal arrays arranged in x-direction. The scintillator crystal layers 2B, 2C and 2D also are formed of scintillator crystals arranged in a two-dimensional matrix form having 32 crystals in x-direction and 32 crystals in y-direction with scintillator crystals b(1, c(1, 1) and d(1, 1) acting as the bases, respectively. In each of the scintillator crystal layers 2A, 2B, 2C and 2D, transmission members t are formed also between adjacent scintillator crystals. Therefore, each of the scintillator crystals is surrounded by the transmission members t. The thickness of these transmission members t is about 25 μm. The gamma rays correspond to the radiation in this invention.

The scintillator crystal layers 2A, 2B, 2C and 2D provided for the scintillator 2 have first reflectors r extending in x-direction and second reflectors s extending in y-direction. Both these reflectors r and s are inserted in gaps between the scintillator crystals arranged.

The scintillator 2 is constructed of scintillator crystals suitable for detection of gamma rays and arranged in three dimensions. That is, the scintillator crystals are formed of $Lu_{2(1-X)}Y_{2X}SiO_5$ (hereinafter called LYSO) diffused with Ce. Each of the scintillator crystals, irrespective of the scintillator crystal layers, is a rectangular parallelepiped which is, for example, 1.45 mm long in x-direction, 1.45 mm wide in y-direction, and 4.5 mm high in z-direction. Of the surfaces of the scintillator 2, the four side surfaces continuous with the light guide 4 are covered with reflective film not shown. The photodetector 3 is the multi-anode type, which can determine positions relating to x and y of incident fluorescence.

The light guide 4 is provided in order to guide the fluorescence generated in the scintillator 2 to the photodetector 3. Therefore, the light guide 4 is optically coupled to the scintillator 2 and photodetector 3. A plurality of connecting terminals 3p are provided on a bottom surface of the photodetector 3 remote from the scintillator 2. These connecting terminals 3p are connected to a bleeder unit 16 to be described hereinafter.

Figure 2:
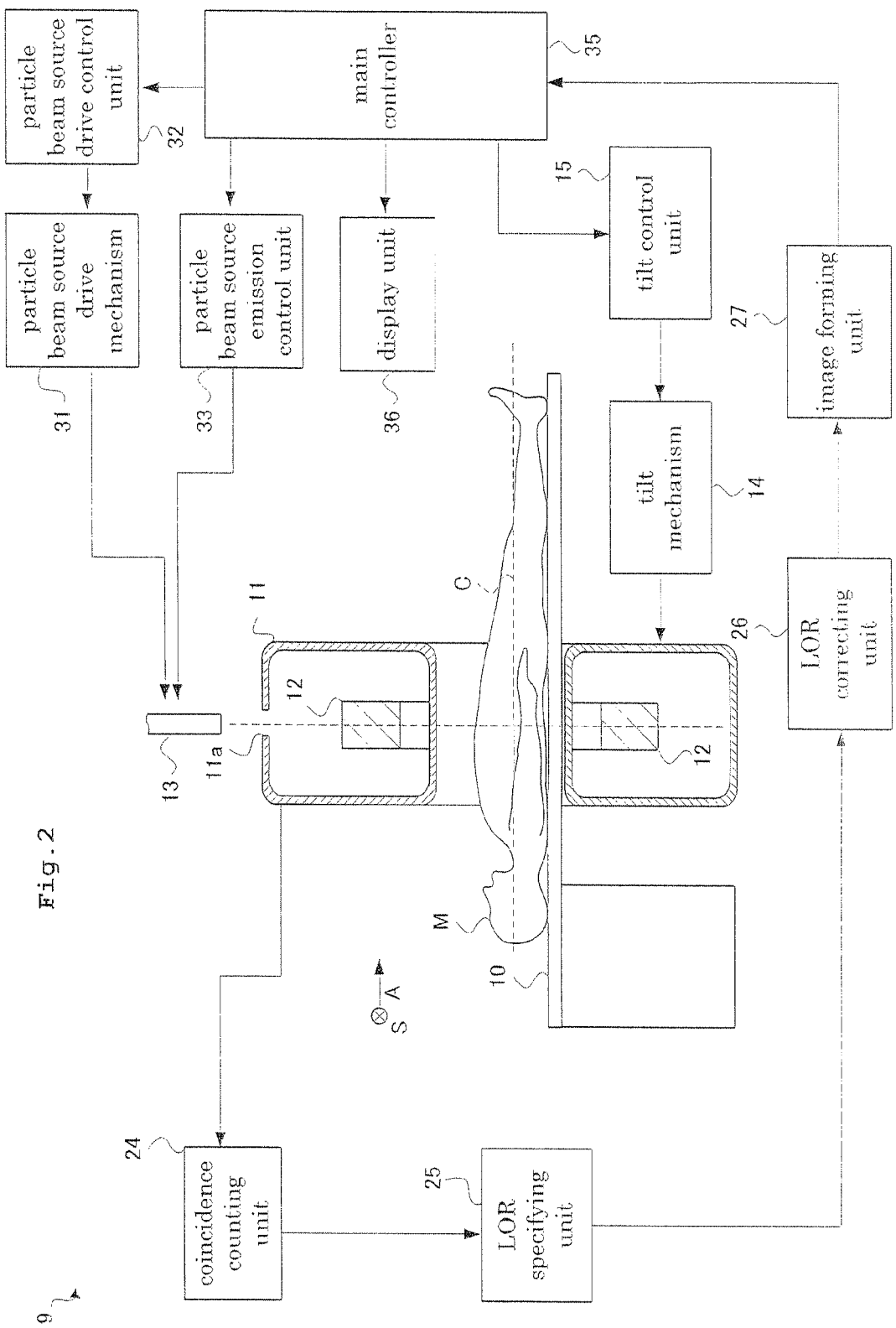
FIG. 2 is a functional block diagram illustrating a construction of a particle radiotherapy apparatus according to Embodiment 1.

Next, a particle radiotherapy apparatus 9 according to Embodiment 1 will be described. FIG. 2 is a functional block diagram illustrating a construction of a particle radiotherapy apparatus according to Embodiment 1. As shown in FIG. 2, the particle radiotherapy apparatus 9 according to Embodiment 1 includes a top board 10 for supporting a patient M, a gantry 11, and an elliptic detector ring 12 mounted inside the gantry 11. The elliptic detector ring 12 corresponds to the detector ring in this invention.

The gantry 11 has a slit 11a formed therein in order to secure a passage for a particle beam. Details of this slit 11a will be described hereinafter.

The particle radiotherapy apparatus 9 further includes various components to acquire sectional images of the patient M. Specifically, the particle radiotherapy apparatus 9 includes a coincidence counting unit 24 for receiving gamma ray detection signals from the elliptic detector ring 12, which signals indicate detected positions, detected strengths and detected times of gamma rays, and carrying out coincidence counting of annihilation gamma ray pairs, an LOR specifying unit 25 for specifying an LOR, to be described hereinafter, from two gamma ray detection data determined to be an annihilation gamma ray pair by the coincidence counting unit 24, an LOR correcting unit 26 for correcting the LOR, and an image forming unit 27 for forming radiation sectional images of a site of interest.

The particle radiotherapy apparatus 9 according to Embodiment 1 has a particle beam source 13 for emitting a particle beam. The particles emitted from the particle beam source 13 are protons or carbon nuclei, for example, but are not limited to these. This particle beam source 13 is driven by a particle beam source drive mechanism 31, and is capable of revolving movement about a base axis C extending along the body axis direction A of the patient M. This particle beam source drive mechanism 31 is controlled by a particle beam source drive control unit 32. Emission of particles from the particle beam source 13 is controlled by a particle beam source emission control unit 33. The particle beam source 13 is revolved about the body axis of the patient M while the direction of particle emission from the particle beam source 13 is changed. Specifically, the particle beam source 13 emits a particle beam in a direction toward the base axis C irrespective of the revolving movement. That is, the particle beam source 13 will emit the particle beam toward one point belonging to the base axis C irrespective of the revolving movement. The particle beam emitted from the particle beam source 13 is introduced into the interior of the gantry 11 by passing through the above-mentioned slit 11a.

The particle radiotherapy apparatus 9 according to Embodiment 1 has a tilt mechanism 14 for tilting the elliptic detector ring 12, and a tilt control unit 15 for controlling this. The tilt control unit corresponds to the detector ring tilting device in this invention.

The particle radiotherapy apparatus 9 according to Embodiment 1 further includes a main controller 35 for carrying out overall control of the various control units, and a display unit 36 for displaying radiation sectional images. This main controller 35 is formed of a CPU, which executes various programs to realize the coincidence counting unit 24, LOR specifying unit 25, LOR correcting unit 26, image forming unit 27, particle beam source drive control unit 32 and particle beam source emission control unit 33.

Figure 3:
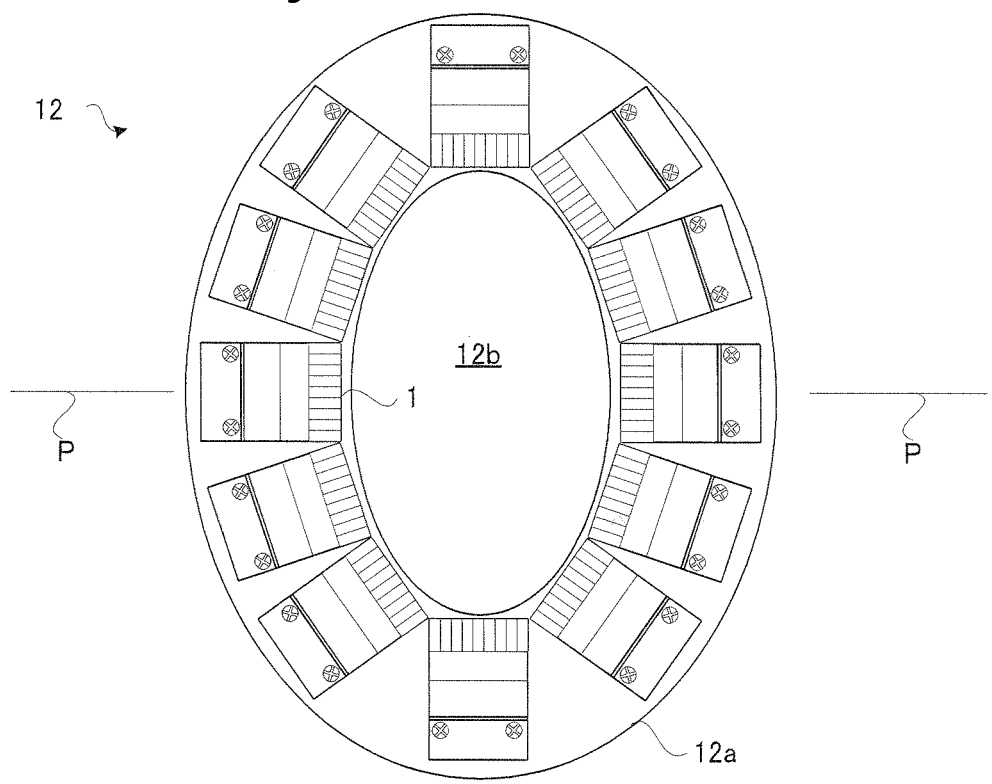
FIG. 3 is a plan view illustrating a construction of an elliptic detector ring according to Embodiment 1.

Next, the construction of the elliptic detector ring 12 according to Embodiment 1 will be described. As shown in FIG. 3, elliptic detector ring 12 has an elliptic type elliptic plate 12a with an elliptic type through-hole formed centrally thereof. Radiation detectors 1 are annularly arranged along this elliptic plate 12a to form the elliptic detector ring 12. Therefore, the elliptic detector ring 12 has an elliptic opening 12b at the center. The radiation detectors 1 have the planes of incidence all arranged to face the opening 12b of the elliptic detector ring 12. The elliptic detector ring 12 has an elliptic shape which is vertically long. P in the drawing indicates the short axis of the elliptic detector ring 12 having the elliptic shape.

Figure 4:
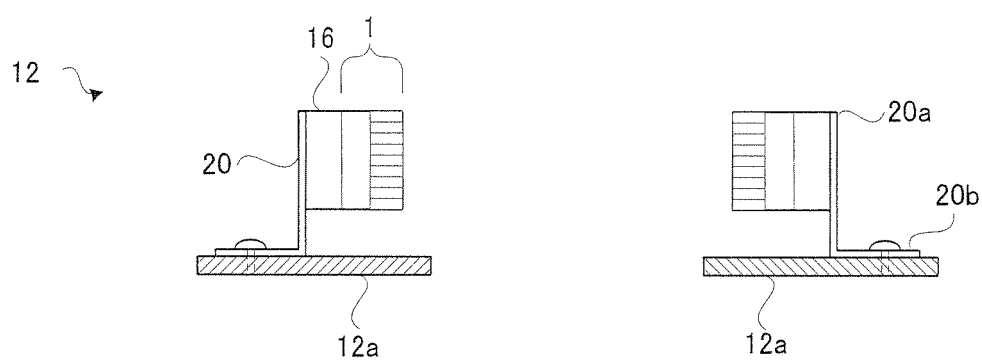
FIG. 4 is a sectional view illustrating the construction of the elliptic detector ring according to Embodiment 1.

FIG. 4 is a sectional view of the elliptic detector ring 12 according to Embodiment 1. This sectional view is a sectional view of the elliptic detector ring 12 cut along the direction of extension of the opening thereof. As shown in FIG. 4, the radiation detectors 1 are provided with bleeder units 16 for supplying electric power thereto. A first radiation detector and bleeder unit 16 are rigidly held together by an L-shaped holder 20. The holder 20 has a main plate 20a for fixing the bleeder unit 16, and an auxiliary plate 20b for fixing the holder 20 itself to the elliptic plate 12a. The bleeder unit 16 is fixed to the elliptic plate 12a through the holder 20.

Figure 5:
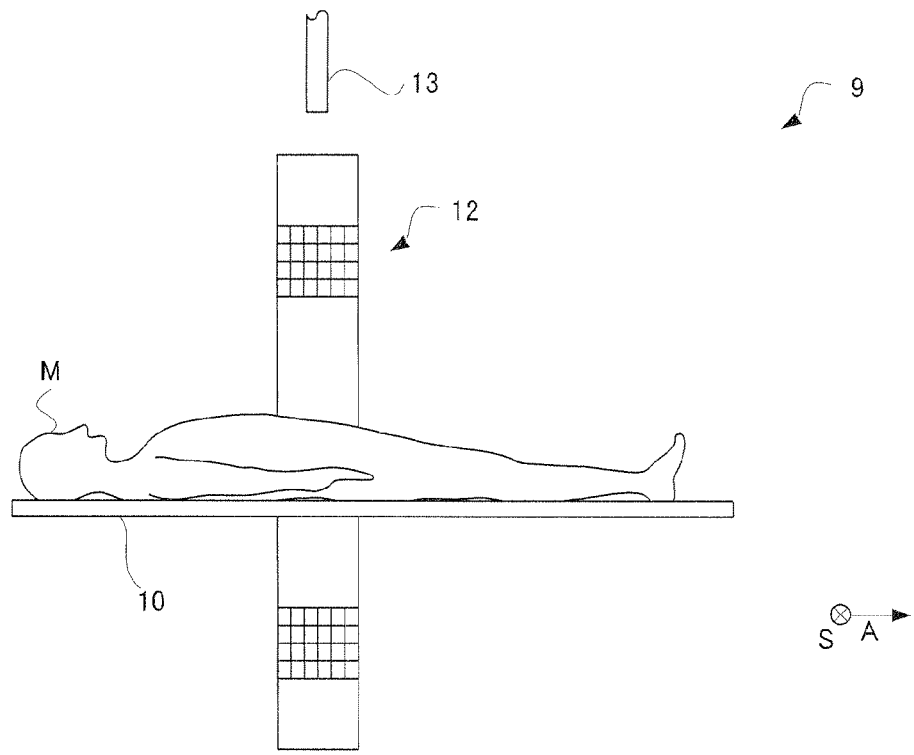
FIG. 5 is a sectional view illustrating the construction of the particle radiotherapy apparatus according Embodiment 1.

Next, changes in tilting of the elliptic detector ring 12 will be described, which is the most salient characteristic of the particle radiotherapy apparatus 9 according to the construction in Embodiment 1. The elliptic detector ring 12 is constructed to have a changeable tilt angle. FIG. 5 shows an initial state before use of the particle radiotherapy apparatus 9 according to the construction in Embodiment 1. The elliptic detector ring 12 is not tilted at this time, with the radiation detectors provided for the elliptic detector ring 12 being all in the same position in the body axis direction A of the patient M. The position of the elliptic detector ring 12 in the non-tilt state is, for example, in strict agreement with the course of the particle beam B to be emitted from the particle beam source 13. That is, in the initial state, no particle beam B is emitted from the particle beam source 13.

Figure 6:
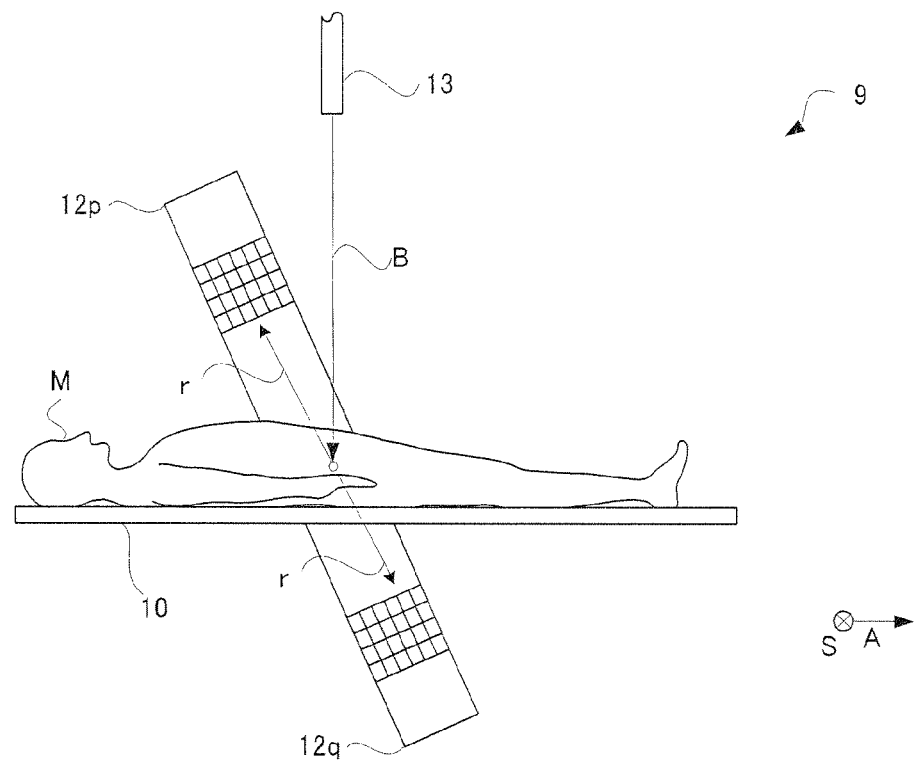
FIG. 6 is a sectional view illustrating the construction of the particle radiotherapy apparatus according to Embodiment 1.

From this initial state, as shown in FIG. 6, the elliptic detector ring 12 is tilted under control of the tilt control unit 15 to have the upper end 12p of the elliptic detector ring 12 tilt forward in the body axis direction A of the patient M. The lower end 12q of the elliptic detector ring 12 is tilted rearward in the body axis direction A of the patient M. The body axis direction A of the patient M is in agreement with the direction of extension of the top board 10 according to Embodiment 1. In this state, the positional relationship between the particle beam source 13 and elliptic detector ring 12 has been changed from the initial state, and the elliptic detector ring 12 is not present in the course of the particle beam B emitted from the particle beam source 13. In such a state, the particle beam B emitted from the particle beam source 13 bypasses the elliptic detector ring 12 to reach the patient M. The upper end 12p of the elliptic detector ring 12 at this time is tilted forward in the body axis direction A of the patient M. The tilt in this direction is called a forward tilt for expedience.

The particle beam is converted into an annihilation gamma ray pair r in the body of the patient M. Since the directions of movement of gamma rays forming this gamma ray pair are 180° opposite directions, there can be a case in which, for example, one of the gamma rays advances forward and upward of the top board 10, and the other of the gamma rays advances rearward and downward of the top board 10. Thus, according to the construction in Embodiment 1, since the elliptic detector ring 12 is tilted relative to the particle beam, the annihilation gamma ray pair can be detected without providing two detector rings as in the conventional construction.

Figure 17:
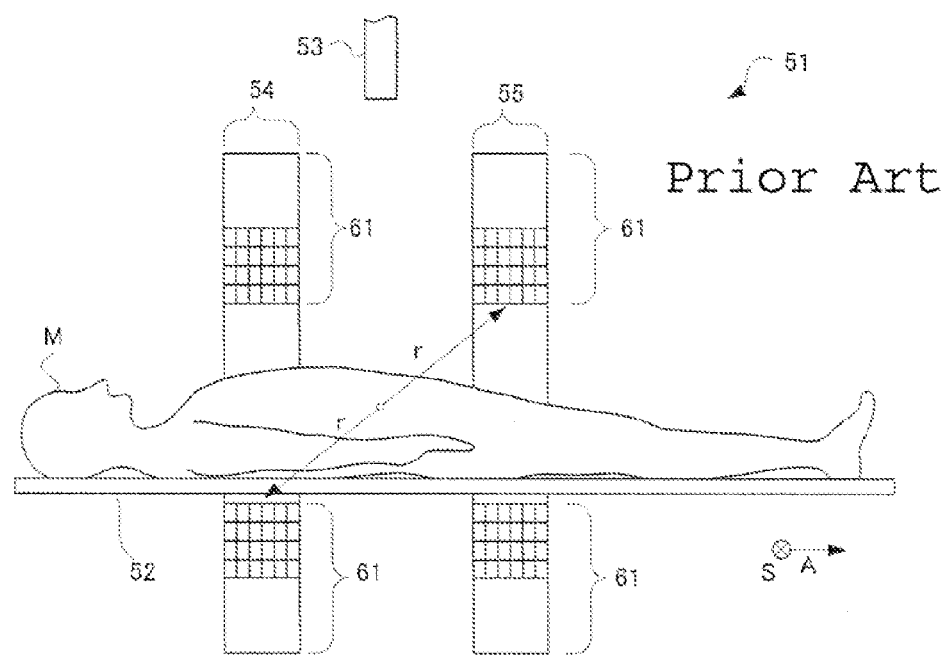
FIG. 17 is a sectional view illustrating the construction of the conventional particle radiotherapy apparatus.

Moreover, according to the construction of Embodiment 1, as will be seen from a comparison between FIG. 6 and FIG. 17 showing the conventional construction, the annihilation gamma ray pair r are incident on the detector ring at an angle close to the right angle. With such construction, the annihilation gamma ray pair r incident on the detector ring pass reliably through central parts of the scintillators 2 provided for the radiation detectors 1. Thus, the construction in Embodiment 1 has a higher sensitivity for detection of gamma rays than the conventional construction.

Figure 7:
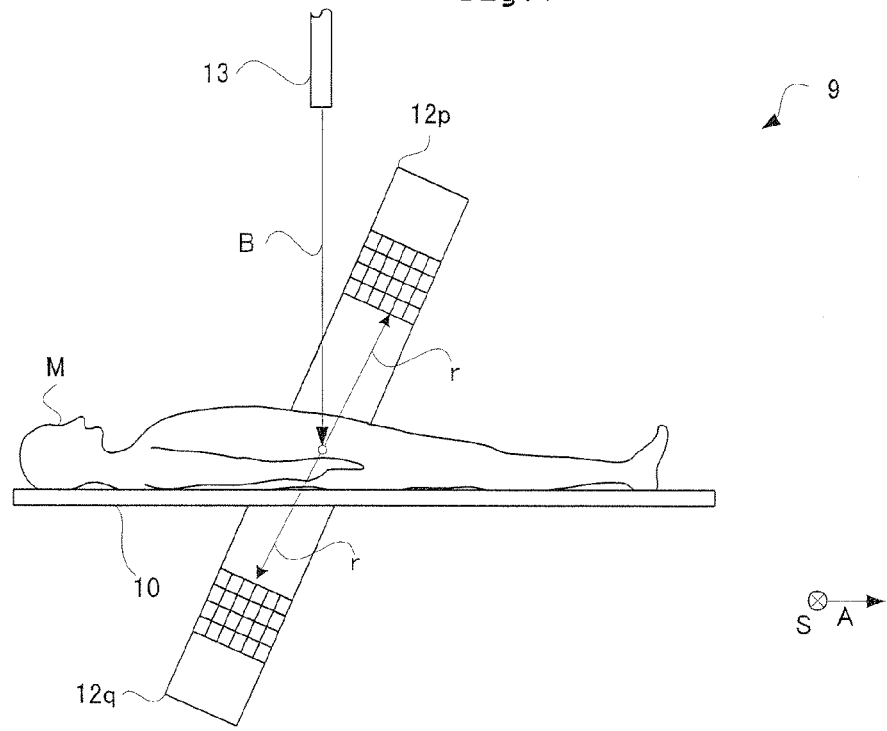
FIG. 7 is a sectional view illustrating the construction of the particle radiotherapy apparatus according to Embodiment 1.

As shown in FIG. 7, the elliptic detector ring 12 can also be tilted under control of the tilt control unit 15 to have the upper end 12p of the elliptic detector ring 12 tilt rearward in the body axis direction A of the patient M. In this case, the lower end 12q of the elliptic detector ring 12 is tilted forward in the body axis direction A of the patient M. Thus, the tilt control unit 15 can cause a tilt also in the reverse direction.

It is predicted that various nuclides are generated at points inside the body of the patient M where the particle beam lost energy. The energies and characteristics of the radiation released by decay thereof are varied. It is possible that single photons which are not annihilation gamma ray pairs are released. Such single photons may be detected by the elliptic detector ring 12. Such single photons cause noise when mapping positions of action of the particle beam using the annihilation gamma ray pairs. However, since tilting of the elliptic detector ring 12, including also the tilting direction, can be changed freely according to the construction of Embodiment 1, the tilt angle of the elliptic detector ring 12 can be changed according to the mode of medical treatment, to secure an optimal S/N ratio. For example, the tilt shown in FIG. 6 may provide a better S/N ratio than the tilt showed in FIG. 7.

Furthermore, it is possible that an intermediate state between the state of FIG. 6 and the state of FIG. 7 provides a better S/N ratio. There can be a case where, for example, the tilt angle is better in the initial state. If the tilt angle is in the initial state, as shown in FIG. 5, the particle beam B will not reach the patient. However, even if the tilt angle is in the initial state, annihilation gamma ray pairs are detectable. That is, the elliptic detector ring 12 may be tilted before emitting the particle beam B from the particle beam source 13, the particle beam B being emitted in this state, and the elliptic detector ring 12 may be returned to the position of the initial state after stopping emission of the particle beam B. Consequently, annihilation gamma ray pairs can be detected while emitting the particle beam B to the patient M. Nuclides which release annihilation gamma rays are generated at points where the particle beam lost energy. However, this does not necessarily emit annihilation gamma ray pairs immediately. Therefore, by returning the elliptic detector ring 12 to the position in the initial state and starting detection of annihilation gamma ray pairs while the nuclides which release annihilation gamma ray pairs remain, the annihilation gamma ray pairs may be detected in a state of good S/N ratio.

In the above description, the elliptic detector ring 12 is moved to a predetermined position, and then annihilation gamma ray pairs are detected. The construction in Embodiment 1 is not limited to this. That is, the particle beam B may be emitted to detect annihilation gamma ray pairs while the elliptic detector ring 12 is in tilting movement. In the particle radiotherapy apparatus 9 according to Embodiment 1, when the elliptic detector ring 12 reaches a predetermined prohibition angle, emission of the particle beam B from the particle beam source 13 is prohibited. Consequently, the particle beam B may be emitted to detect annihilation gamma ray pairs while the elliptic detector ring 12 is in tilting movement.

The short axis P of the elliptic detector ring 12 is shown in FIG. 3. This short axis P is a central axis of tilting of the elliptic detector ring 12. That is, the elliptic detector ring 12 is tilted while maintaining the position of the short axis P. Incidentally, the long axis of the elliptic detector ring 12 will tilt with tilting of the elliptic detector ring 12.

Figure 8:
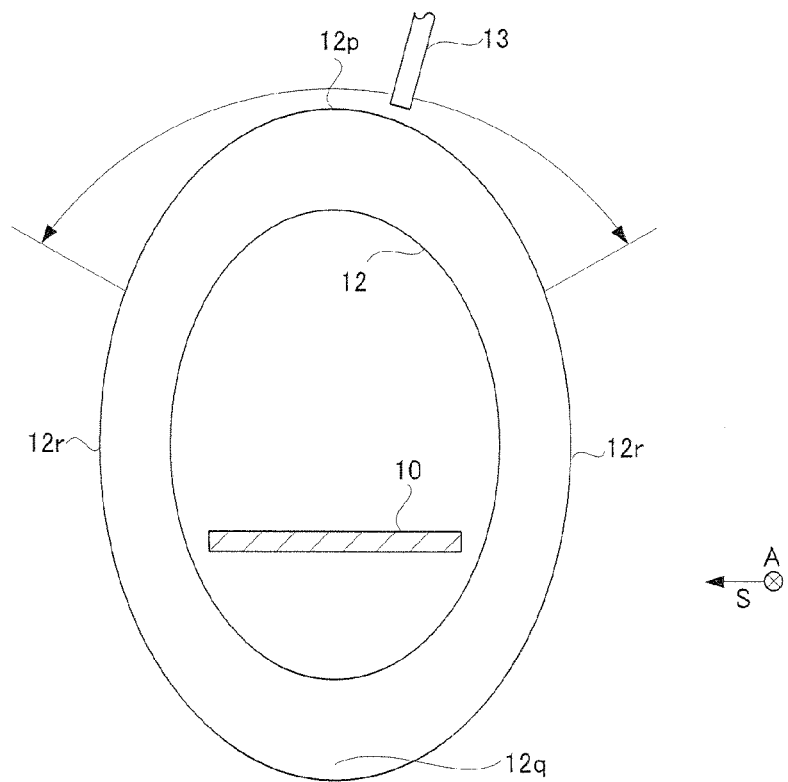
FIG. 8 is a sectional view illustrating revolution of a particle beam source according to Embodiment 1.

Next, revolving movement of the particle beam source 13 will be described. FIG. 8 is a sectional view illustrating revolution of the particle beam source according to Embodiment 1. As shown in FIG. 8, the particle beam source 13 can make revolving movement about the body axis of the patient M by revolving from a position vertically upward of the elliptic detector ring 12. The particle beam source 13 can make a circle about the body axis of the patient M. However, a particle beam is not always emitted during the revolving movement.

When the elliptic detector ring 12 is tilted, the upper end 12p and lower end 12q of the elliptic detector ring 12 will move a long distance. However, opposite lateral ends 12r of the elliptic detector ring 12 in the body side direction A of the patient M only rotate and do not move. That is, the effect of changing the position of the elliptic detector ring 12 by tilting the elliptic detector ring 12 diminishes as it approaches the opposite lateral ends 12r in the body side direction A of the patient M. As the particle beam source 13 is revolved to the vicinity of the short axis P of the elliptic detector ring 12, the particle beam B emitted from the particle beam source 13 will soon interfere with the elliptic detector ring 12. Thus, the particle beam source 13 is constructed to emit the particle beam while being revolved adjacent the long axis of the elliptic detector ring 12.

Figure 9:
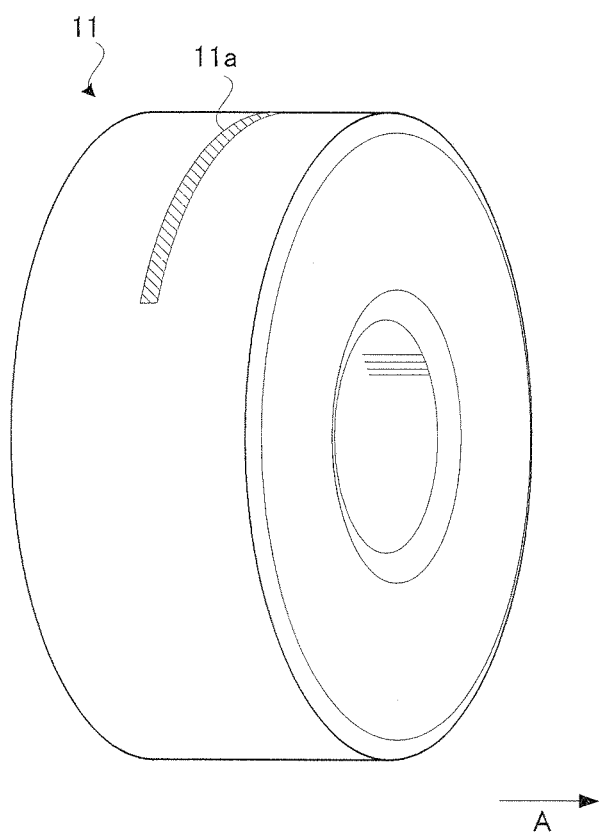
FIG. 9 is a perspective view illustrating a construction of a gantry according to Embodiment 1.

For this revolving movement of the particle beam B, the slit 11a is formed in the gantry 11. That is, as shown in FIG. 9, the gantry 11 has the slit 11a extending so as to circumvent the body axis of the patient M. The shape of this slit 11a is in agreement with the locus of the particle beam B in revolving movement.

Figure 10:
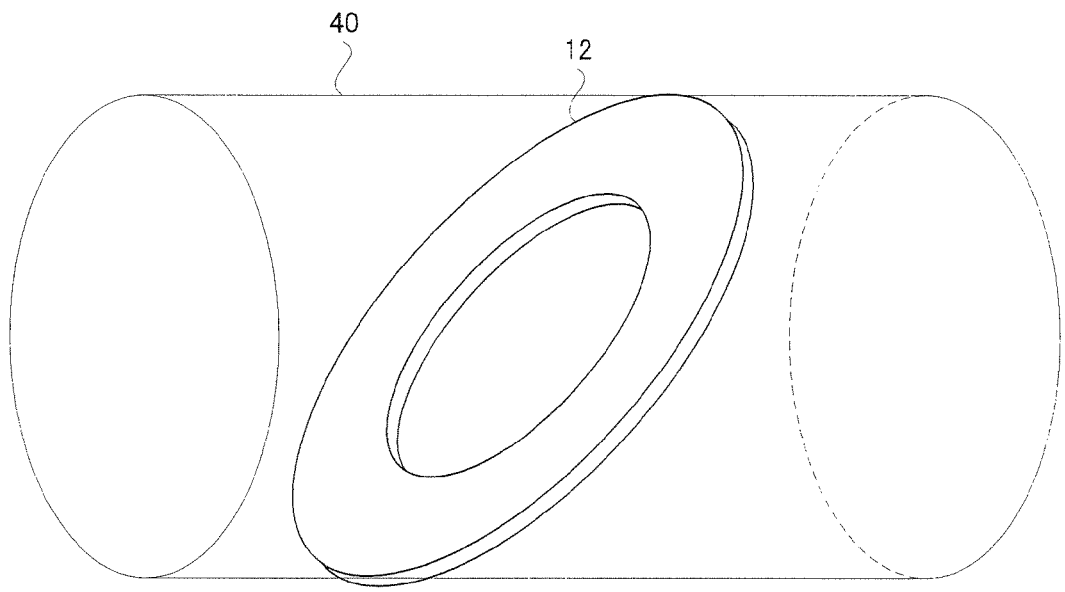
FIG. 10 is a perspective view illustrating the elliptic detector ring according to Embodiment 1.
Figure 11:
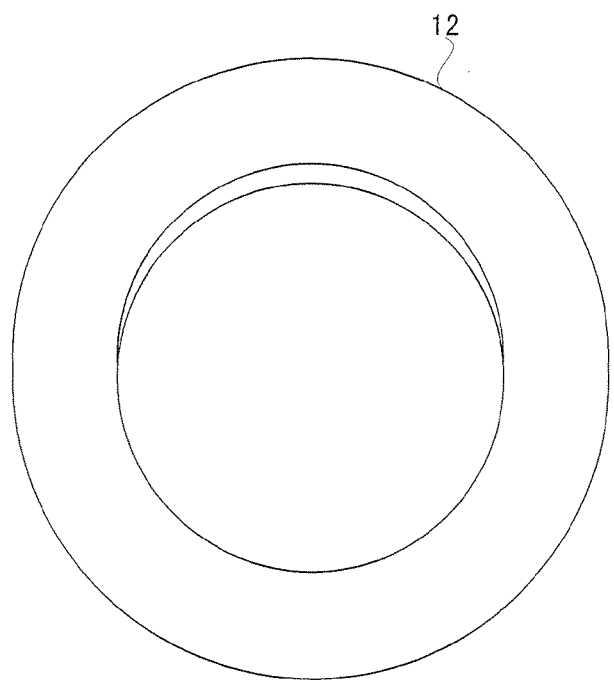
FIG. 11 is a perspective view illustrating the elliptic detector ring according to Embodiment 1.

The elliptic detector ring 12 is shaped to meet predetermined conditions. Elliptic conditions adopted for the elliptic detector ring 12 will be described next. FIG. 10 is a perspective view illustrating the elliptic detector ring according to Embodiment 1. FIG. 10 shows a state where the elliptic detector ring 12 is tilted to a maximum angle. At this time, the side edge of the elliptic detector ring 12 is included in the surface of an imaginary cylinder 40 extending in a direction corresponding to the body axis direction A of the patient M. When the elliptic detector ring 12 is seen from a front of the cylinder 40 at this time, as shown in FIG. 11, the elliptic detector ring 12 presents a shape of a precise circle.

The radiation detectors 1 provided for the elliptic detector ring 12 are arranged along the shape of the elliptic detector ring 12. Therefore, when the elliptic detector ring 12 is tilted to the maximum angle, each of the radiation detectors 1 provided for the elliptic detector ring 12 will be arranged along the cylinder 40.

With such construction, also when the elliptic detector ring 12 is tilted to the maximum angle, the elliptic detector ring 12 will never interfere with the patient M. When the elliptic detector ring 12 is tilted, the upper part of elliptic detector ring 12 will descend and approach the patient M. However, also when the elliptic detector ring 12 is tilted to the maximum angle as mentioned above, the elliptic detector ring 12 will never interfere with the patient M, provided that the shape and maximum tilt angle of the elliptic detector ring 12 are set based on the imaginary cylinder 40 as described above.

Figure 12:
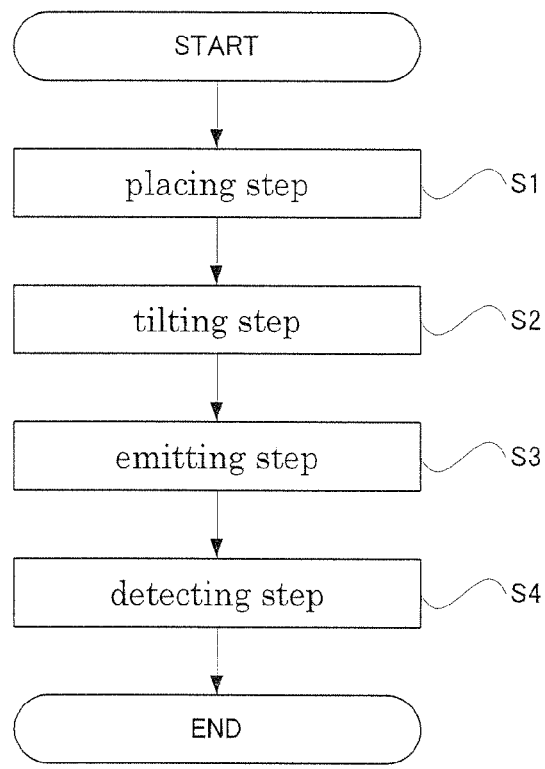
FIG. 12 is a flow chart illustrating operation of the particle radiotherapy apparatus according to Embodiment 1.

Next, operation of the particle radiotherapy apparatus 9 having such construction will be described. As shown in FIG. 12, operation of the particle radiotherapy apparatus 9 includes a placing step S1 for placing the patient M on the top board 10, a tilting step S2 for tilting the elliptic detector ring 12, an emitting step S3 for emitting a particle beam B from the particle beam source 13 toward the patient M, and a detecting step S4 for detecting annihilation gamma rays generating from the particle beam. Particulars of each of these steps will be described in order hereinafter.

First, the patient M is placed on the top board 10 (placing step S1). Then, the operator causes movement of the top board 10 along the body axis direction A of the patient M to set the lesion of the patient M to a position in the passage of the particle beam B emitted from the particle beam source 13. Next, the operator gives instructions for the elliptic detector ring 12, whereupon the elliptic detector ring 12 is tilted to a tilt angle and in a tilting direction as instructed by the operator (tilting step S2). The particle radiotherapy apparatus 9, with the elliptic detector ring 12 set to the predetermined tilt angle, is permitted to emit the particle beam B, and stands by until the operator gives instructions. When the operator instructs emission of the particle beam, the particle beam B is emitted from the particle beam source 13 (emitting step S3). Then, annihilation gamma ray pairs generating from the particle beam B are detected by the elliptic detector ring 12 (detecting step S4). The image forming unit 27 creates a distribution map of the annihilation gamma rays detected from the patient M based on detection data outputted from the elliptic detector ring 12. This is displayed on the display unit 36, which enables the operator to check whether the particle beam B reaches the lesion properly. In this way, the operation of the particle radiotherapy apparatus 9 according to Embodiment 1 is completed. The above tilting step S2 and emitting step S3 may be executed at the same time. That is, the particle beam B may be emitted while the elliptic detector ring 12 is in tilting movement.

Next, data processing of the particle radiotherapy apparatus 9 according to Embodiment 1 will be described referring to FIG. 2. An annihilation gamma ray pair produced inside the patient M will be detected by certain of the radiation detectors 1 provided for the elliptic detector ring 12. The elliptic detector ring 12 outputs detection data resulting from detection of gamma rays to the coincidence counting unit 24. When detection data derived from two different scintillator crystals is included in a time window having a predetermined duration, the coincidence counting unit 24 regards this as being due to an annihilation gamma ray pair, and counts the number of times thereof. This is a count number.

The LOR specifying unit 25 deduces the exiting directions of the annihilation gamma ray pair. That is, the detection data regarded as coincident by the coincidence counting unit 24 includes positional information indicating which scintillator crystals emitted fluorescence. The LOR specifying unit 25 deduces an LOR (Line of Response) which is a line segment linking these two scintillator crystals, and outputs the LOR and a count number corresponding thereto to the LOR correcting unit 26.

As a characteristic arrangement of the construction in Embodiment 1, it is noted that the detection data outputted from the elliptic detector ring 12 includes information on the tilting direction and tilt angle of the elliptic detector ring 12.

The LOR corrector 26 makes a correction of the LOR to remove the influence of tilting of the elliptic detector ring 12. According to the construction in Embodiment 1, tilting of the elliptic detector ring 12 will change a relative positional relationship between the elliptic detector ring 12 and the patient M. Besides, the LOR shows only a relative position in the elliptic detector ring 12 of a position of occurrence of the annihilation gamma ray pair. With such construction, since the directions indicated by the LOR changes with the tilt angle of the elliptic detector ring 12, it is impossible, after all, to determine where the annihilation gamma rays have occurred. However, according to the construction of Embodiment 1, a correction is made to incline the LOR virtually based on the information on the tilting direction and tilt angle of the elliptic detector ring 12, which information is included in the detection data. Thus, the influence of changes in the tilting of the elliptic detector ring 12 has been removed from data outputted from the LOR correcting unit 26. Therefore, the construction in Embodiment 1 can determine the position of occurrence of the annihilation gamma ray pair even if the elliptic detector ring 12 is tilted. This corrected LOR and a count number corresponding thereto are outputted to the image forming unit 27.

Based on corrected LORs and count numbers corresponding thereto, the image forming unit 27 maps an occurrence distribution of annihilation gamma ray pairs in a sectional plane the patient M. A sectional image formed in this way is displayed on the display unit 36. The occurrence distribution of annihilation gamma ray pairs displayed enables monitoring of the site where the particle beam lost energy in the sectional plane of the patient M. In this way, it can be checked whether the particle beam in the particle radiotherapy apparatus 9 reliably acts on the lesion of the patient M.

As described above, the construction in Embodiment 1 includes the tilt control unit 15 for reversibly tilting the elliptic detector ring 12. Consequently, the elliptic detector ring 12 is tilted relative to the top board 10. More particularly, the upper end 12p of the elliptic detector ring 12 is tilted in one direction in the direction of extension of the top board 10. The lower end 12q of the elliptic detector ring 12 is tilted in a direction opposite to the one direction in the direction of extension of the top board 10. The particle beam source 13 emits a particle beam B toward the top board 10. Therefore, the elliptic detector ring 12 cannot be disposed in a position to interfere with travel of this particle beam B. The construction in Embodiment 1 can tilt the elliptic detector ring 12 relative to the top board 10. This means that the positional relationship between the elliptic detector ring 12 and particle beam B is changeable. Therefore, since the elliptic detector ring 12 can be moved away from the particle beam B by tilting the elliptic detector ring 12 according to Embodiment 1, it is possible to provide the particle radiotherapy apparatus 9 which can detect annihilation radiation while emitting the particle beam B.

Figure 18:
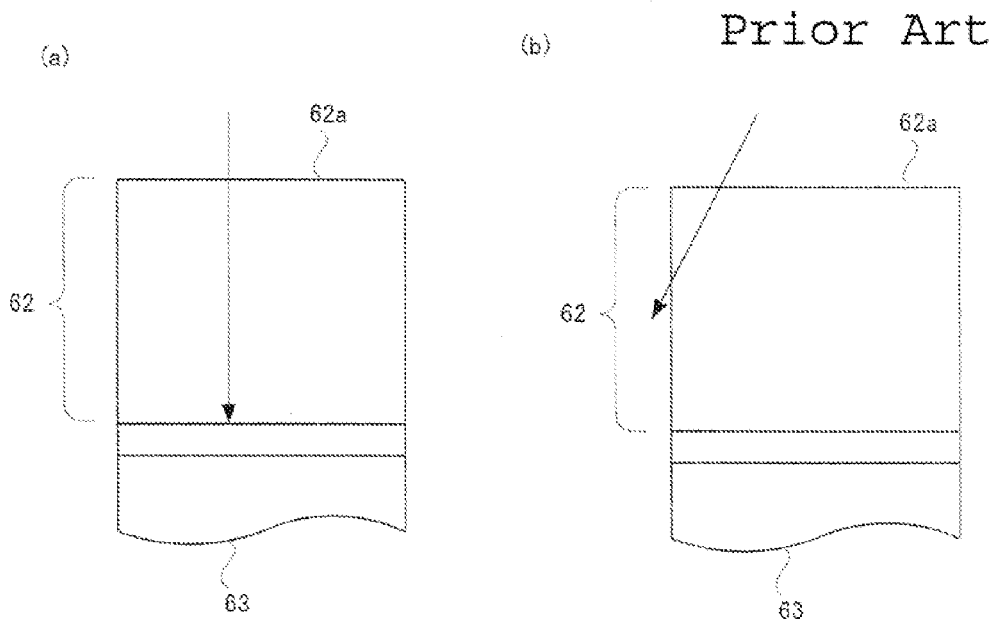
FIG. 18 is a sectional view illustrating the construction of the conventional particle radiotherapy apparatus.
Figure 19:
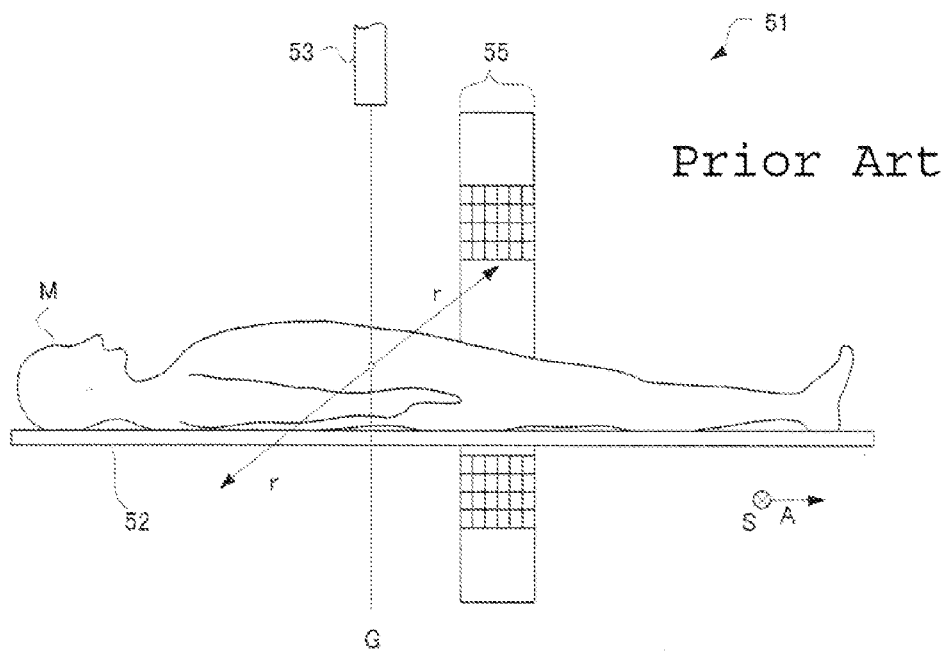
FIG. 19 is a sectional view illustrating the construction of the conventional particle radiotherapy apparatus.

Moreover, annihilation gamma ray pairs are detected with the single elliptic detector ring 12. Then, annihilation gamma ray pairs occurring inside the elliptic detector ring 12 will be detected. In other words, all annihilation gamma ray pairs will impinge on the single elliptic detector ring 12 at substantially right angles. This inhibits the lowering of the sensitivity for detection described using FIG. 18.

According to Embodiment 1, the upper end 12p and lower end 12q of the elliptic detector ring 12 are tilted in opposite directions. Consequently, the predetermined area (lesion area of the patient M) can always be located inside the opening of the elliptic detector ring 12 irrespective of the tilting of the elliptic detector ring 12. The particle radiotherapy apparatus 9 can create a map of occurrence distribution of annihilation gamma ray pairs for the inside of the opening of the elliptic detector ring 12. The lesion area of the patient M being located inside the opening of the elliptic detector ring 12 irrespective of the tilting of the elliptic detector ring 12 means that an occurrence distribution of annihilation gamma ray pairs in the lesion area of the patient M is acquirable also while emitting the particle beam. That is, according to the construction in Embodiment 1, it is not necessary to provide two detector rings as in the prior art, but annihilation gamma ray pairs can be detected fully only by providing the single elliptic detector ring 12. The particle radiotherapy apparatus 9 with manufacturing cost sharply reduced as compared with the prior art can be provided since the manufacturing cost of the particle radiotherapy apparatus 9 depends heavily on the number of radiation detectors 1 mounted in the elliptic detector ring 12.

According to the construction in Embodiment 1, the elliptic detector ring 12 has an elliptic shape which is vertically long. Moreover, at a predetermined tilt angle, the radiation detectors 1 provided for the elliptic detector ring 12 are in a characteristic arrangement. That is, the radiation detectors 1 are arranged along the imaginary cylinder 40. The shape provided by obliquely cutting the cylinder 40 whose extending direction corresponds to the top board 10 agrees with the elliptic shape of the elliptic detector ring 12. And the radiation detectors 1 provided for the elliptic detector ring 12 are also arranged along this imaginary cylinder 40. As the elliptic detector ring 12 is tilted, the upper part and lower part of the elliptic detector ring 12 approach the top board 10. However, according to the construction in Embodiment 1, since the elliptic detector ring 12 is vertically long, the elliptic detector ring 12 reliably remains out of contact with the patient M.

The construction in Embodiment 1 can provide the particle radiotherapy apparatus 9 which can image the lesion of the patient M reliably only by keeping in agreement the lesion of the patient M and the short axis P of the elliptic detector ring 12. That is, according to the construction in Embodiment 1, the position of the short axis P of the elliptic detector ring 12 is constant irrespective of tilting of the elliptic detector ring 12. Thus, the short axis of the elliptic detector ring 12 will always be located inside the opening of the elliptic detector ring 12 irrespective of the tilting. Therefore, the construction in Embodiment 1 can provide the particle radiotherapy apparatus 9 which can image the lesion of the patient M more simply and reliably.

The construction in Embodiment 1 can provide the particle radiotherapy apparatus 9 with high sensitivity for detection of annihilation gamma ray pairs. It is predicted that various nuclides are generated at points inside the body of the patient M where the particle beam lost energy. The energies and characteristics of the radiation released by decay thereof are varied. It is possible that single photons which are not annihilation gamma ray pairs are released. Such single photons may be detected by the elliptic detector ring 12. These cause noise when imaging positions of action of the particle beam using the annihilation gamma ray pairs. However, according to the construction in Embodiment 1, tilting of the elliptic detector ring 12, including also the tilting direction, can be optimized. Specifically, the particle beam may be emitted while tilting the elliptic detector ring 12, for the purpose of determining a tilt of the elliptic detector ring 12. When a desired tilt of the elliptic detector ring 12 has been determined, the particle beam B may be emitted while maintaining the tilt angle.

This invention is not limited to the foregoing construction, but may be modified as follows:

(1) The construction in Embodiment 1 described above relates to particle radiotherapy which emits a particle beam to the patient M. The particle radiotherapy apparatus 9 of this invention can be used also as an ordinary PET (Positron Emission Tomography) apparatus. That is, the patient M is medicated with a radioactive substance labeled with a positron emission type radioisotope, and a distribution thereof inside the patient M can be imaged.

(2) The scintillator crystals in the foregoing embodiment are formed of LYSO. In this invention, the scintillator crystals may be formed of other materials such as GSO ($Gd_2SiO_5$). This modification can provide a radiation detector manufacturing method that can provide less expensive radiation detectors.

(3) In the foregoing embodiment, the scintillator has four scintillator crystal layers. This invention is not limited to this. For example, a scintillator formed of one scintillator crystal layer may be applied to this invention. In addition, the number of scintillator crystal layers can be adjusted freely according to the use of the radiation detectors.

(4) In the foregoing embodiment, the fluorescence detector is in form of a photomultiplier tube. This invention is not limited to this. Instead of the photomultiplier tube, a photodiode, an avalanche photodiode or the like may be used.

Figure 13:
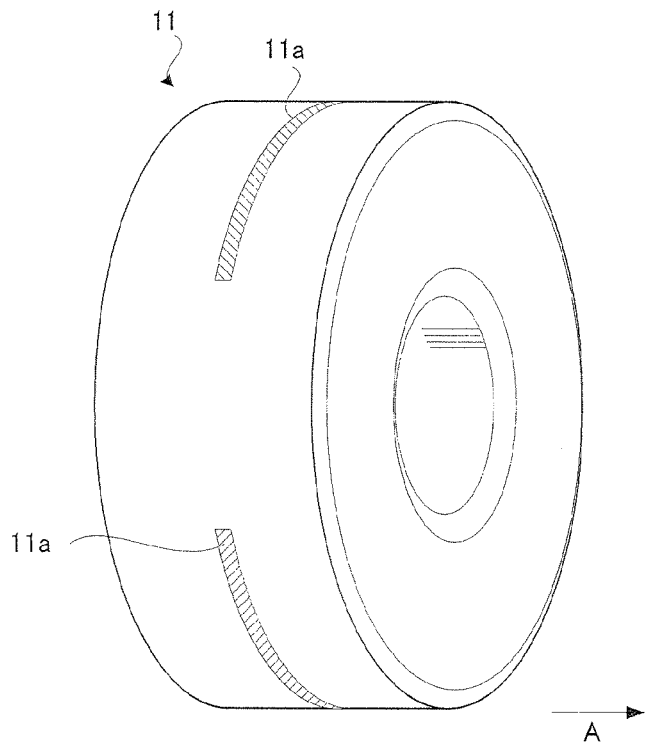
FIG. 13 is a perspective view illustrating a construction of a gantry according to one modification of this invention.
Figure 14:
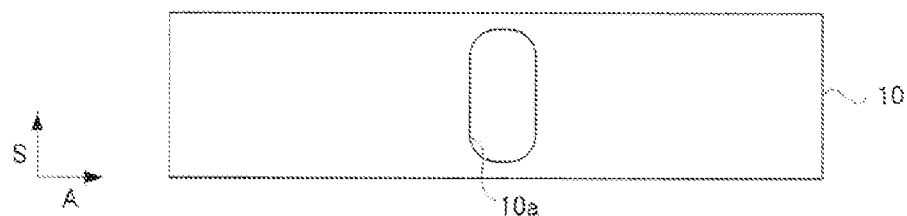
FIG. 14 is a perspective view illustrating a construction of a top board according to the one modification of this invention.
Figure 14:
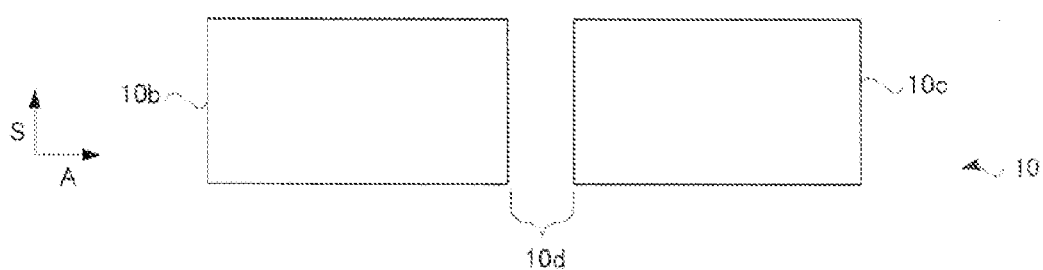
Figure 15:
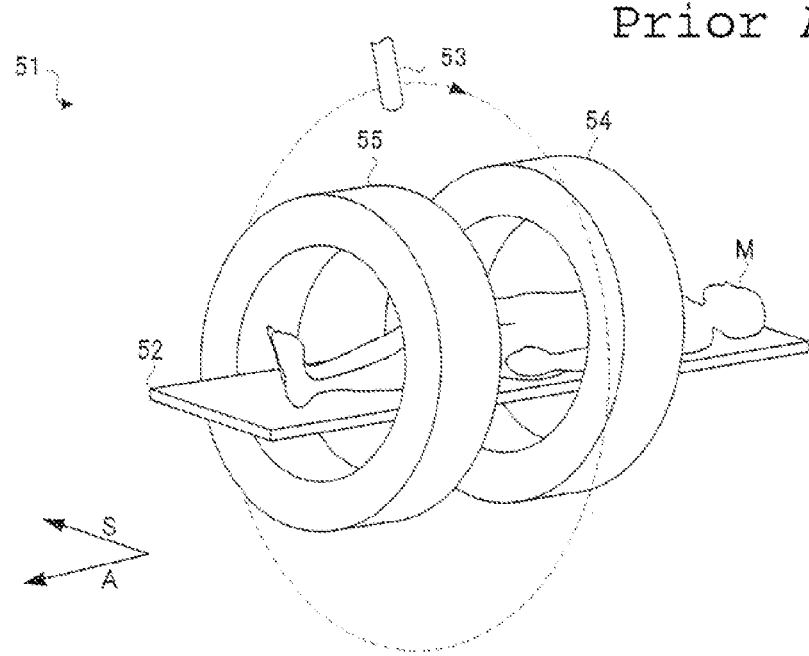
FIG. 15 is a perspective view illustrating a construction of a conventional particle radiotherapy apparatus.
Figure 16:
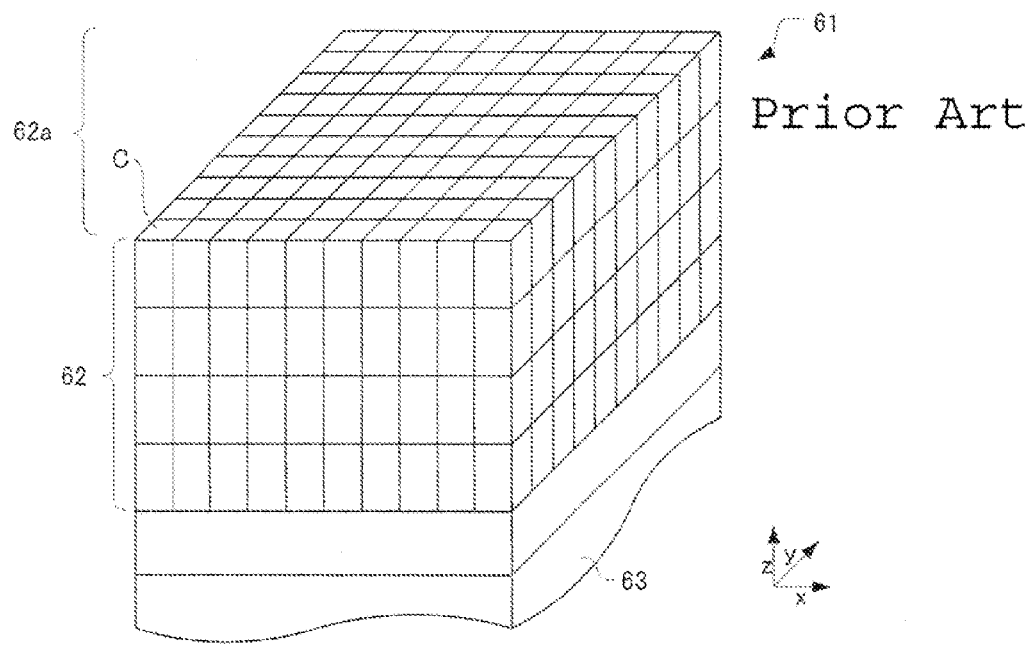
FIG. 16 is a perspective view illustrating the construction of the conventional particle radiotherapy apparatus.

(5) In the foregoing embodiment, the gantry 11 has a single slit. This invention is not limited to this. As shown in FIG. 13, for example, the gantry 11 may have two, upper and lower, slits 10a. Consequently, even when the particle beam source 13 has moved below the top board 10, it can emit a particle beam toward the patient M. In this case, as shown in FIG. 14, the top board 10 may have a bore 10a for passage of the particle beam. The top board 10 may be halved into a first fragment 10b and a second fragment 10c, with a slit 10d formed between first fragment 10b and second fragment 10c for passage of the particle beam. With this construction, the particle beam is emitted reliably to the patient M without passing through the top board 10.

INDUSTRIAL UTILITY

As described above, this invention is suitable for medical radiographic apparatus.

The invention claimed is:

1. A particle radiotherapy apparatus comprising a detector ring constructed of an annular arrangement of radiation detectors formed by laminating, in one direction, scintillators with planes of incidence for receiving radiation and converting the radiation into fluorescence, light guides for receiving and transmitting the fluorescence, and photodetectors for detecting the fluorescence, and in addition thereto, an elongated top board inserted in an opening of the detector ring, and a particle beam emitting device for emitting a particle beam, the particle radiotherapy apparatus further comprising:
a detector ring tilting device for reversibly tilting the detector ring relative to the top board;
wherein the detector ring tilting device is arranged to tilt an upper end of the detector ring in one direction in a direction of extension of the top board, and to tilt a lower end of the detector ring in a direction opposite to the one direction in the direction of extension of the top board.

2. The particle radiotherapy apparatus according to claim 1, wherein:
the detector ring has on elliptic shape; and
when the detector ring is tilted to a predetermined tilt angle, the radiation detectors provided for the detector ring are arranged along an imaginary cylinder having a direction of extension in agreement with the top board.

3. The particle radiotherapy apparatus according to claim 2, wherein:
the detector ring tilting device is arranged to tilt the detector ring about a central axis provided by a short axis of the detector ring having the elliptic shape; and
a position of the short axis of the detector ring is constant irrespective of tilting of the detector ring.

4. The particle radiotherapy apparatus according to claim 3, wherein the detector ring is arranged to detect radiation resulting from the particle beam while being tilted by the detector ring tilting device.

5. The particle radiotherapy apparatus according to claim 3, wherein the detector ring is arranged to detect radiation resulting from the particle beam after being tilted by the detector ring tilting device and in a state of maintaining the tilt angle.

6. The particle radiotherapy apparatus according to claim 2, wherein the detector ring is vertically long.

7. The particle radiotherapy apparatus according to claim 2, wherein the detector ring is arranged to detect radiation resulting from the particle beam while being tilted by the detector ring tilting device.

8. The particle radiotherapy apparatus according to claim 2, wherein the detector ring is arranged to detect radiation resulting from the particle beam after being tilted by the detector ring tilting device and in a state of maintaining the tilt angle.

9. The particle radiotherapy apparatus according to claim 1, wherein the detector ring is vertically long.

10. The particle radiotherapy apparatus according to claim 9, wherein:
the detector ring tilting device is arranged to tilt the detector ring about a central axis provided by a short axis of the detector ring having the elliptic shape; and
a position of the short axis of the detector ring is constant irrespective of tilting of the detector ring.

11. The particle radiotherapy apparatus according to claim 9, wherein the detector ring is arranged to detect radiation resulting from the particle beam while being tilted by the detector ring tilting device.

12. The particle radiotherapy apparatus according to claim 9, wherein the detector ring is arranged to detect radiation resulting from the particle beam after being tilted by the detector ring tilting device and in a state of maintaining the tilt angle.

13. The particle radiotherapy apparatus according to claim 1, wherein the detector ring is arranged to detect radiation resulting from the particle beam while being tilted by the detector ring tilting device.

14. The particle radiotherapy apparatus according to claim 1, wherein the detector ring is arranged to detect radiation resulting from the particle beam after being tilted by the detector ring tilting device and in a state of maintaining the tilt angle.

* * * * *